United States Patent [19]

Calvani et al.

[11] Patent Number: 4,832,492
[45] Date of Patent: May 23, 1989

[54] HETERODYNE MICHELSON INTERFEROMETER FOR POLARIZATION MEASUREMENTS

[75] Inventors: Riccardo Calvani, Pino Torinese; Renato Caponi; Francesco Cisternino, both of Torino, all of Italy

[73] Assignee: CSELT - Centro Studi E Laboratori Telecommunicazioni SPA, Turin, Italy

[21] Appl. No.: 81,485

[22] Filed: Aug. 4, 1987

[30] Foreign Application Priority Data

Aug. 8, 1986 [IT] Italy ................................ 67643 A/86

[51] Int. Cl.$^4$ .................................................. G01B 9/02
[52] U.S. Cl. ........................................ 356/349; 356/351
[58] Field of Search ........................ 356/349, 351, 358

[56] References Cited

U.S. PATENT DOCUMENTS 4,506,388  3/1985  Monerie et al.
4,633,715  1/1987  Monchalin ......................... 356/358

OTHER PUBLICATIONS

R. Calvani et al, "A Heterodyne Mach–Zehnder Polarimeter for Real-Time Polarization Measurement", vol. 54, No. 2, 15 May 1985, pp. 63–67 (Optics Communications).

R. Calvani et al, "A Fast Heterodyne Interferometer for Real-Time Fibre Polarimetry", vol. XIII, No. 5, Oct. 1985 (CSET Technical reports), pp. 313–316.

H F Hazebrock et al, "Automated Laser Interferometric Ellipsometry and Precision Reflectometry", 8056 Journal of Physics E. Scientific Instruments, vol. 16 (1983), Jul., No. 7, Dorking, GB, pp. 654–661.

R. M. A. Azzam et al, "Ellipsometry and Polarized Light", North-Holland Publishing Company-Amsterdam-New York-Oxford, 1977.

Primary Examiner—Vincent P. McGraw
Assistant Examiner—S. A. Turner
Attorney, Agent, or Firm—Herbert Dubno

[57] ABSTRACT

The interferometer makes use of an acousto-optic device to perform a frequency shift of the beam sent along one of the interferometer branches, so as to allow the determination of the state of polarization by heterodyne radiofrequency detection. The acousto-optic device can be inserted downstream of the device for splitting the beam emitted by the source into the two beams sent along the two interferometer branches, or it can also act as the beam splitter.

18 Claims, 2 Drawing Sheets

HETERODYNE MICHELSON INTERFEROMETER FOR POLARIZATION MEASUREMENTS

FIELD OF THE INVENTION

Our present invention relates to polarization measurements and, more particularly, to a Michelson interferometer for determining the state of polarization of a radiation emerging from a transparent or reflecting body.

BACKGROUND OF THE INVENTION

It is known that a body transmitting or reflecting a light radiation can introduce variations in the state of polarization of the light radiation. Knowledge of the state of polarization of the radiation emerging from the body is of importance to completely characterize the body in respect of its optical properties, and is essential when exploiting interference or beats between radiations, since these phenomena occur only when the radiations are equally or correspondingly polarized.

Applications include well-known applications of classical optics, optical coherent or heterodyne telecommunications (based on beats) and optical fiber sensors or gyroscopes, requiring the use of fibers maintaining a determined state of polarization.

A polarized radiation can be characterized by electromagnetic field components in a reference system with orthogonal axes x, y. Considering the electrical field alone, the two components are given by:

$$Ex = a1 \cos \omega t \quad Ey = a2 \cos(\omega t + \psi) \tag{1}$$

where $a1$, $a2$ are the amplitudes of the two components and $\psi$ is the relative phase. To determine the state of polarization it is necessary to measure the ratio $a2/a1$ between the two amplitudes and phase $\psi$, whose sign defines the rotation direction on the polarization image, described on plane Ex, Ey as t varies. From these two values further information can be derived necessary to characterize the body under test, e.g. polarization beat length, in case of single-mode optical fibers.

It is also to be noted that the state of polarization can vary in time. In case of optical waveguides, this usually occurs owing to variable mechanical and thermal stresses which modify their optical properties.

In order to determine time-varying polarization state, interferometric techniques have also proved to be useful. An example based on a Mach-Zehnder interferometer has been described by us in the article A heterodyne Mach-Zehnder polarimeter for real-time polarization measurement, Optics Communications, Vol. 54, No. 2, 15 May 1985, and in the paper "A fast heterodyne interferometer for real-time fiber polarimetry" presented at IOOC-ECOC '85, Venice, October 1985.

Yet this solution requires all the light beams inside the device to be coplanar, to avoid systematic errors which depend also on the polarization state to be determined and which hence cannot be eliminated by a simple instrument calibration.

A Michelson interferometer is intrinsically free from these disadvantages, since the light beam emitted from the source is split into two beams which are back-reflected; such beams are obviously coplanar, and the distance between the beam-splitter and the mirrors can be maintained very short.

An example of apparatus for measuring the state of polarization, based on a Michelson interferometer, is described in *Ellipsometry and polarized light,* by R.m.A. Azzam and N. M. Bashara, North-Holland Publishing Company, 1977, pages 262-265, and in the paper *Automated laser interferometric ellipsometry and precision reflectometry,* by H. F. Hazebroek and W. M. Visser, Journal of Physics, Section E, Vol. 16, 1983, pages 654-661.

These documents disclose an ellipsometer, i.e. a device for measuring the polarization state of radiation reflected by the surface of a body. In that ellipsometer, polarized radiation is split by a beam splitter into two fractions. One fraction is sent towards the body under test and reflected onto a mirror by which it is reflected back onto the body and hence to the splitter; the other, acting as a reference beam, is sent to a corner reflector and therefrom to the splitter. The corner reflector is oscillated so as to change by Doppler effect the frequency of the beam sent back towards the splitter in the reference branch. The two beams are recombined by the splitter into a single beam containing both frequencies. The components parallel and perpendicular to the incidence plane on the body under test are separated and sent to different detectors. A microprocessor obtains the required information from the intensities of the beat signals supplied by the detectors.

A system of this kind has a number of disadvantages. More particularly, the corner reflector position is critical, since it has to be chosen so as to make reference beam coincide with one of the two reflector self-polarizations, in order to maintain the reference beam polarization; there are moving parts, which always entail reliability problems; the system operates at low frequency (200 Hz) so that it does not allow detection of polarization fluctuations which are very rapid.

OBJECT OF THE INVENTION

It is the object of our invention to provide an interferometer which overcomes these drawbacks and which does not present moving parts and operates at high frequencies (from some tens to some hundreds of MHz), so that it can follow even very short fluctuations of the state of polarization.

SUMMARY OF THE INVENTION

The present invention provides a Michelson interferometer for measuring the polarization state of a light beam outgoing from a transparent or reflecting body, which comprises:

a monochromatic light source a light-beam splitting-recombining device, which receives a light beam coming from the source, splits it into a pair of partial beams, sends said partial beams along two branches of the interferometer, ending at respective mirrors perpendicular to the propagation direction of the partial beams, and receives and recombines into a single beam the partial beams reflected by such mirrors;

means inserted in one of such branches and arranged to give the partial beam sent along said branch a predetermined linear polarization state, so as to obtain a reference beam;

means arranged to shift in frequency the other partial beam, which presents the state of polarization to be determined; and means arranged to analyze in polarization the recombined beam, to generate electrical beams representing the beats among equally polarized components of the recombined beam and to obtain the state of polarization from the intensities and the relative phase of such electrical signals.

According to the invention, the frequency-shifting means comprises an acousto-optic device driven by a radiofrequency signal, the device receiving a beam having the same frequency as the beam generated by the source, emitting a first beam having the same frequency as the received beam and a second beam whose frequency differs from that of the received beam by a value equal to the frequency of the driving signal, and sending at least the second beam towards one of the mirrors. The acousto-optical device is arranged so as to be traversed again by the reflected beam and consequently to emit a third and fourth beams, at least one of said third and fourth beams having different frequency from the received beam and being recombined with the reference beam.

BRIEF DESCRIPTION OF THE DRAWING

The above objects, features and advantages of our invention will become more readily apparent from the following description, reference being made to the accompanying drawing in which.

SPECIFIC DESCRIPTION

Figure 1:
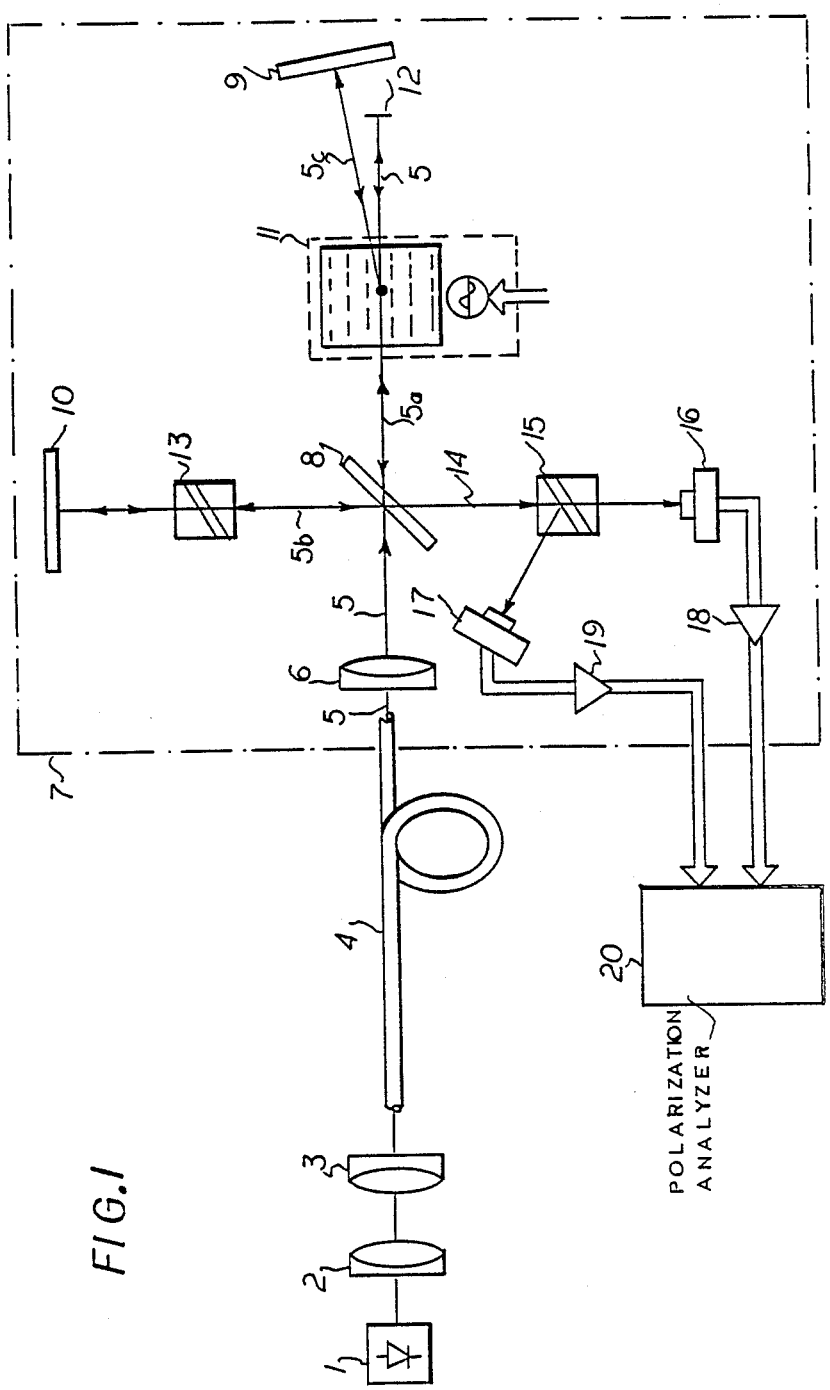
FIG. 1 is a diagram of an interferometer according to a first embodiment of the invention.

The drawing shows the application of the invention to the measurement of the state of polarization at the output of a single-mode optical fiber which is located between the source of the radiation used for the measurement and the interferometer. This arrangement is the one that better takes into account the fact that the fiber length may exceed source coherence length, so that, if the fiber were to be inserted in an interferometer branch, precise phase relations between the two radiations to be recombined might no longer exist.

With reference to FIG. 1, a light-beam source 1, e.g. a semiconductor laser without particular spectral requirements, emits a light beam which is collimated and focussed at the entrance of a single-mode optical fiber 4 through a suitable optical system schematized by lenses 2, 3.

Beam 5, outgoing from fiber 4 and containing the information on the state of polarization to be determined, is collimated by a further optical system 6 and sent to a Michelson interferometer, denoted as a whole by 7. The interferometer comprises a beam splitting-recombining device 8, splitting beam 5 into a transmitted partial beam 5a and a reflected partial beam 5b, and to branches, ending respectively at mirrors 9, 10.

Beam fraction 5a sent along the first branch enters an acousto-optic device 11, mounted with its optical axis oriented at the optimal angle (i.e. the Bragg angle) with respect to beam incidence direction and driven by a suitable radiofrequency electrical signal (e.g. a 40 MHz signal).

Device 11, as known, lets through input beam 5a unchanged in frequency and direction, and emits a second beam 5c, with frequency equal to the sum or difference between the frequency of the optical input radiation and that of the electrical driving signal. The direction of beam 5c is determined by the Bragg diffraction law, i.e. it is such that deflection 5a–5c undergone by the beam owing to acousto-optic interaction is equal to twice the Bragg angle. By the arrangement shown in FIG. 1, the second beam 5c has a frequency equal to the sum of said two frequencies. Beam 5a is intercepted by a suitable absorbing screen 12, while beam 5c reaches mirror 9, perpendicular to its propagation direction, and is hence back-reflected towards acousto-optic device 11.

Device 11 shifts in frequency and deviates again the received beam, operating now on beam 5c. The beam deviated and shifted twice in frequency, outgoing from device 11, is exactly superimposed on incoming beam 5a and arrives at beam splitting-recombining device 8. The outgoing beam which propagates unchanged can be intercepted by a device analogous to screen 12 or, by a suitable component arrangement, it can be let out from the interferometer without affecting the measurement.

Beam fraction 5b launched into the second branch of interferometer 7 is caused to pass through a device 13 giving the beam a well-defined state of polarization; device 13 can be e.g. a Glan-Taylor prism arranged to transmit the linear polarization component at 45° C. alone. The polarized beam outgoing from prism 13 impinges orthogonally onto mirror 10, is back-reflected, traverses prism 13 again, emerging still linearly polarized at 45°, and arrives again at splitting-recombining device 8. This beam constitutes a reference beam.

Splitting-recombining device 8 forms a beam 14 comprising the transmitted fraction of the reference beam and the reflected fraction of the frequency-shifted beam. Beam 14 is sent to a polarization analyzing device 15, e.g. a second Glan-Taylor prism with axes coinciding with those of splitting-recombining device 8. Beats among equally polarized components of the two radiations of recombined beam 14 are present at the two outputs of prism 15. These beats are detected by detectors 16, 17, whose output signals are suitably amplified in amplifiers 18, 19, and are fed to measurement and/or display devices 20 (e.g. a vector voltmeter and/or an oscilloscope operating in x-y mode) allowing measurement and/or display of ratio Ex/Ey and of phase difference $\psi$. Suitable processing means, not shown, will obtain the desired fiber characteristics from measurements of two or more polarization states obtained under different conditions.

Detector signals have amplitude proportional to a1 and a2 and relative phase $\psi$. In fact, supposing for simplicity sake that the reflected and transmitted beams outgoing from device 8 have equal intensities, the beam arriving at device 8 after reflection onto mirror 8 will be characterized by an electric field $$Emx = k.Eox.\exp[i(\omega + 2\Omega)t] Emy = k.Eoy.\exp\{i[\omega + 2\Omega]t + \psi\} \quad (2)$$

where: $Eox = h.a1$ and $Eoy = h.a2$ are the intensities before the double passage through device 11; k, h, are constants taking into account losses due to the efficiency of said device and to the beam splitting in device 8, respectively, and $\Omega$ is the frequency of the signal driving device 11.

The reference beam, linearly polarized at 45°, is characterized by an electric field $$Erx = Ery = Eo/\sqrt{2}) \cdot \exp[i(\omega t + \psi R)] \quad (3)$$

where Eo, $\psi$ R are given by $$E_o = E_{ox}^2 + E_{oy}^2 - 2E_{ox}E_{oy}\cos\psi R = \operatorname{arctg}[E_{oy}\sin\psi/(E_{ox} + E_{oy}\cos\psi)] \quad (4)$$

The two fields are superimposed at the output of device 8 giving rise to a sum of the homonymous components (2), (3) along axes x, y. Prism 15 will send the component polarized along axis x towards detector 16 and the component polarized along axis y towards detector 17.

The signals outgoing from the detectors are proportional to the intensities (i.e. the squares) of the detected field components. Consequently, once eliminated the d.c. components of the currents outgoing from detectors 16, 17 by filtering in amplifiers 18, 19, the corresponding electrical signals Sx, Sy sent to measurement and/or display devices 20 are proportional to the beats between field homonymous components (2), (3). Sx, Sy are hence oscillating electrical signals at a frequency equal to the difference between the frequencies of the two beams, and will have respectively intensity $$S_x = K.E_o.E_{ox}\cos(2\Omega t - \psi R) \quad S_y = K.E_o.E_{oy}\cos(2\Omega t - \psi R + \psi) \quad (5)$$

From these relations one can see immediately that the phase difference between the two signals is actually $\phi$ and that, taking into account the values of Eox, Eoy, their amplitudes are proportional to a1 and a2 respectively.

Figure 2:
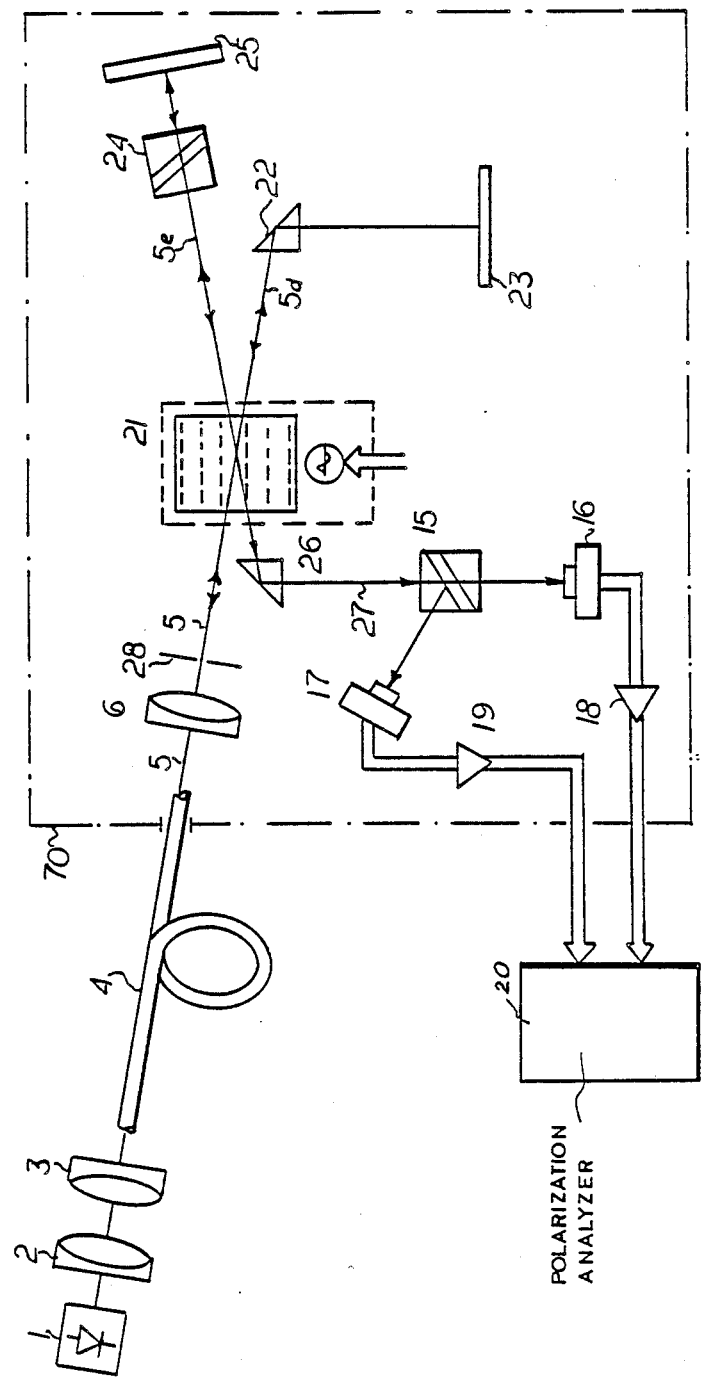
FIG. 2 is a diagram of a second embodiment of the invention.

In the embodiment of FIG. 2, where the interferometer is denoted by 70, beam 5 collimated by optical system 6 is directly sent to acousto-optic device 21, having the tasks of both device 11 and splitting-recombining device 8 of FIG. 1. Beam 5 enters device 21 at the Bragg angle to the optical axis of the device. Non-deviated outgoing beam 5d is collected by a total-reflection prism 22 and sent onto a mirror 23, orthogonal to the propogation direction of the beam reflected by the prism. This reflected beam is hence sent back towards prism 22 and device 21. Deviated and frequency-shifted outgoing beam 5e is on the contrary send to Glan-Taylor prism 24 and to mirror 25, which are identical to prism 13 and mirror 10 of FIG. 1, respectively, and is reflected towards device 21.

Prism 22 allows a fair spatial separation between beams 5d, 5e and an easy location of prism 24 and mirror 25, notwithstanding the small angle between the two beams: this contributes to maintaining the longitudinal interferometer dimensions limited.

Device 21, owing to its arrangement, causes on beams reflected by mirrors 23, 25 a frequency shift analogous to that performed on incident beam 5. Hence, beam 5d will give rise to a beam with frequency $\omega - \Omega$ (deviated) and a beam with frequency $\omega + \Omega$ (non deviated; beam 5e (with frequency $\omega + \Omega$) will give rise to a beam with frequency $\omega + \Omega$ (non-deviated) and a beam with frequency $\omega + \Omega 2$ (deviated). The non-deviated beam deriving from beam 5e and the deviated beam deriving from beam 5d are superimposed into a recombined beam 27 and are sent, through a second total-reflection prism 26 acting like prism 22, to Glan-Taylor prism 15 for polarization analysis and subsequent heterodyne detection through detectors 17, 18. The non-deviated beam deriving from beam 5d and the deviated beam deriving from beam 5e are superimposed upon beam 5 and can be exploited for an alignment check, using e.g. an iris 28 inserted between optical system 6 and device 21. The same iris can be used to prevent the beam from reentering the cavity of a semi-conductor laser, thereby changing the coherence length thereof.

What has been stated above for the embodiment of FIG. 1 applies also to the embodiment of FIG. 2, apart from the fact that the beat takes place between optical frequencies $\omega + \Omega$ and $\omega + \Omega$, and not between frequencies $\omega$ and $\omega + 2\Omega$.

The description above clearly shows that the present invention eliminates the drawbacks of the known device. In fact there are no moving parts, and hence mechanical devices designed to generate motion are no longer necessary; the mirrors in both branches are simple plane mirrors and not composite members like the corner reflector of the prior art, so that no problem arises of critical orientation of the reflecting means with respect to the interferometer plane; finally, with the usual frequencies used to drive device 11 or 21, the electrical signal containing polarization information has a frequency of at least some tens MHz, and hence even very short variations in the state of polarization can be observed.

It is evident that variations are possible without going out of the scope of the invention. E.g., if the state of polarization to be determined is imposed by a transparent body whose thickness is much smaller than source coherence length or by a reflecting sample (as in ellipsometric measurements), the body can be inserted inside the interferometer, in the branch which does not contain prism 13 or 24. In the case described of the measurements on a transmitted beam, the processings necessary to obtain the optical characteristics of the body from the state of polarization ought to be modified so as to take into account, in the formulations, the double crossing of the body by the light beam. This presents no difficulty for a skilled worker in the art.

We claim:

1. A heterodyne Michelson interferometer for measuring a state of polarization of radiation outgoing from a body, comprising:

a monochromatic light-beam source emitting a monochromatic light beam along a path, said body being positioned along said path so that radiation in the form of a light beam from said source is outgoing from said body;

a light-beam splitting and recombining device positioned along said path downstream and provided with means for:

receiving said light beam from said body, splitting the received light beam into a pair of partial beams, sending said partial beams along two path branches, and receiving reflected partial beams from said path branches and recombining the reflected partial beam into a single beam;

respective mirrors positioned at ends of said path branches and perpendicular to the partial beams sent therealong for forming said reflected partial beams and reflecting them back to said light-beam splitting and recombining device for recombination into said single beam;

means in one of said path branches for imparting to the partial beam sent therealong a predetermined linear state of polarization, thereby forming from the partial beam with said predetermined linear state of polarization a reference beam, the other partial beam having said state of polarization to be determined;

means for imparting a frequency shift to said other partial beam and including an acousto-optical device driven by a radiofrequency signal and receiving said other beam having said state of polarization to be determined and emitting a first beam having the same frequency as the other beam received by the acousto-optical device and a second beam whose frequency differs from that of the first beam by a value equal to the frequency of said radiofrequency signal, said acousto-optical device being positioned so that at least said second beam is sent as said other partial beam to the mirror perpendicular thereto, said acousto-optical device also being positioned to be traversed by the second beam as reflected by the last-mentioned mirror so as to emit a third and a fourth beam at least one of which has a frequency different from that of said first beam and is recombined into said single beam with said reference beam; and polarization-analysis means for analyzing said single beam representing the recombination of the reflected partial beams to generate electrical signals representing beats between correspondingly polarized components of the single beam and determining the state of polarization from intensities and relative phase of said signals.

2. The interferometer defined in claim 1 wherein said body is a transparent body.

3. The interferometer defined in claim 1 wherein said body is a reflective body.

4. The interferometer defined in claim 1 wherein said acousto-optical device is located in the path of the other partial beam outgoing from said light-beam splitting and recombining device and is constructed and arranged to recombine said reference beam and the beam recombined therewith after the latter beam has undergone a frequency shift equal to twice the frequency of the radiofrequency signal driving said acousto-optical device.

5. The interferometer defined in claim 1 wherein light-beam splitting and recombining device includes said means for imparting a frequency shift to said other beam, the first and second beams emitted by said acousto-optical device forming said one and said other partial beams, respectively.

6. The interferometer defined in claim 5 wherein said acousto-optical device is mounted so that said monochromatic beam from said source impinges thereon at the Bragg angle to an optical longitudinal axis of said acousto-optical device, said light-beam splitting and recombining device recombining beams whose frequencies are respectively the sum and the difference of the frequency of the monochromatic light beam from said source and that of the radiofrequency signal driving said acousto-optical device.

7. The interferometer defined in claim 5, further comprising respective total-reflection prisms located along a path of one of said partial beams between said acousto-optical device and a respective mirror, and along the path of the recombined beam for respectively sending the respective beams to the respective mirror and to said polarization-analyzing means for increasing spatial beam separation.

8. The interferometer defined in claim 5, further comprising an iris in the path of a beam emerging from said acousto-optical device and incident thereon for effecting an alignment check of components of the interferometer.

9. The interferometer defined in claim 5, further comprising an iris in the path of a beam emerging from said acousto-optical device and incident thereon for preventing a beam emerging from said acousto-optical device from entering said source.

10. The interferometer defined in claim 1 wherein said body is a single-mode glass fiber disposed between said source and said light-beam splitting and recombining device.

11. A heterodyne Michelson interferometer for measuring a state of polarization of radiation outgoing from a body, comprising:

a monochromatic light-beam source emitting a monochromatic light beam along a path, said body being positioned along said path so that radiation in the form of a light beam from said source is outgoing from said body;

a light-beam splitting and recombining device positioned along said path and provided with means for:

receiving said light beam from said body, splitting the received light beam into a pair of partial beams, sending said partial beams along two path branches, receiving reflected partial beams from said path branches and recombining the reflected partial beam into a single beam, and imparting a frequency shift to said other partial beam;

respective mirrors positioned at ends of said path branches and perpendicular to the partial beams sent therealong for forming said reflected partial beams and reflecting them back to said light-beam splitting and recombining device for recombination into said single beam;

means in one of said path branches for imparting to the partial beam sent therealong a predetermined linear state of polarization, thereby forming from the partial beam with said predetermined linear state of polarization a reference beam, the other partial beam having said state of polarization to be determined, said means for imparting a frequency shift to said other partial beam including an acousto-optical device driven by a radiofrequency signal and receiving said other beam having said state of polarization to be determined and emitting a first beam having the same frequency as the other beam received by the acousto-optical device and a second beam whose frequency differs from that of the first beam by a value equal to the frequency of said radiofrequency signal, said acousto-optical device being positioned so that at least said second beam is sent as said other partial beam to the mirror perpendicular thereto, said acousto-optical device also being positioned to be traversed by the second beam as reflected by the last-mentioned mirror so as to emit a third and a fourth beam at least one of which has a frequency different from that of said first beam and is recombined into said single beam with said reference beam; and polarization-analysis means for analyzing said single beam representing the recombination of the reflected partial beams to generate electrical signals representing beats between correspondingly polarized components of the single beam and determining the state of polarization from intensities and relative phase of said signals.

12. In a heterodyne Michelson interferometer for measuring the state of polarization of a radiation outgoing from a transparent or reflecting body, comprising;
   a monochromatic light beam source (1) irradiating said body (4) so that a light beam is outgoing from said body (4);
   a light-beam splitting-recombining device (8; 21), which receives a light beam (5) coming from the body (4), splits it into a pair of partial beams (5a, 5b; 5d, 5e), sends such partial beams (5a; 5b; 5d, 5e) along two branches of the interferometer ending at respective mirrors (9, 10; 23, 25) arranged perpendicularly to the direction of propagation of the partial beams, and receives and recombines into a single beam the partial beams reflected by such mirrors (9, 10; 23, 25);
   means (13; 24) inserted in one of such branches to give the partial beam sent along it a predetermined linear state of polarization, so as to obtain a reference beam;
   means (11, 12) for frequency-shifting the other partial beam, which presents the state of polarization to be determined; and
   means (15, 16, 17, 18, 19, 20) for analyzing in polarization the recombined beam (14; 27), to generate electrical signals representing the beat between the equally polarized components of the recombined beam and to obtain the state of polarization from the intensities and the relative phase of such electrical signals, the improvement wherein:
   the frequency shifting means comprise an acousto-optic device (11, 21) driven by a radiofrequency signal, which device receives a beam (5) presenting the state of polarization to be determined, emits a first beam having the same frequency as the received beam and a second beam whose frequency differs from that of the received beam by a value equal to the frequency of the driving signal, and sends at least the second beam towards one of the mirrors (9, 23), the device (11; 21) being arranged so as to be traversed again by the reflected beam and consequently to emit a third and fourth beam of which one at least has frequency different from that of the received beam and is combined with the reference beam.

13. The improvement defined in claim 12, wherein said acousto-optic device (11) is inserted along the path of the second partial beam (5a) outgoing from the beam splitting device (8) and is arranged so as to recombine such second partial beam with the reference beam after the former has undergone a frequency shift equal to twice the frequency of the signal driving the acousto-optic device (11).

14. The improvement defined in claim 12 wherein said acousto-optic device (21) is inserted along the path of the beam (5) emitted by the source (1) and forms the beam splitting-recombining device, the first and second beams (5d, 5e) emitted by the acousto-optic device (21) forming said first and second partial beams).

15. The improvement defined in claim 14 wherein said acousto-optic device (21) is mounted so that the beam (5) coming from the source (1) impinges thereon at the Bragg angle to its optical longitudinal axis, said device (21) recombining beams whose frequency is the sum and respectively the difference of the frequency of the beam emitted by the source and that of the signal driving the acousto-optic device (21).

16. The improvement defined in claim 14 wherein along the path of one of the partial beams, between the acousto-optical device (21) and the mirror (23), and along the path of the recombined beam, between the acousto-optic device (21) and the means (15) for polarization analysis, total-reflection prisms (22, 26) are located which send such beams towards the mirror (23) and the means (15) for polarization analysis, respectively, and improve the spatial separation between said beams.

17. The improvement defined in claim 14 wherein the acousto-optic device (21) is arranged so as to generate, when traversed again by the partial beams (5d, 5e) after reflection thereof by the mirrors (23, 25), beams having the same frequency as the beam incident thereon and to reflect back such beams along the same path as the incident beam, and in that an iris (28) is provided to intercept such beams for a check of the alignment of the interferometer components and/or to prevent such beams from reentering the source (1).

18. The improvement defined in claim 1 which is used to measure the state of polarization at the output of a single-mode optical fiber (4) arranged between the source (1) and the beam splitting-recombining means (8; 21).

* * * * *